United States Patent [19]

Kozak

[11] Patent Number: 4,888,999
[45] Date of Patent: Dec. 26, 1989

[54] TANK BOTTOM SAMPLING DEVICE

[76] Inventor: Robert J. Kozak, 412 Sheridan Ave., Roselle Park, N.J. 07204

[21] Appl. No.: 254,590

[22] Filed: Oct. 7, 1988

[51] Int. Cl.$^4$ .......................... G01N 1/12; G01N 1/08
[52] U.S. Cl. .............................. 73/864.65; 73/864.62; 73/864.44
[58] Field of Search ........... 73/864.65, 864.63, 864.66, 73/864.44, 864.45, 864.62

[56] References Cited

U.S. PATENT DOCUMENTS

| | | |
|---|---|---|
| 1,996,534 | 4/1935 | Baker . |
| 2,678,563 | 5/1954 | Parrish .................. 73/864.65 |
| 2,865,204 | 12/1958 | Lamb . |
| 3,461,192 | 8/1969 | Di Stasio . |
| 3,791,220 | 2/1974 | Falk et al. ................. 73/DIG. 9 |
| 4,116,247 | 9/1978 | Zanasi ....................... 73/864.44 X |
| 4,305,279 | 12/1981 | Ontek .......................... 73/864.63 X |
| 4,346,519 | 8/1982 | Milo ............................. 73/864.63 X |
| 4,406,171 | 9/1983 | Uebershaer ................... 73/864.62 |
| 4,760,747 | 8/1988 | Fackler ........................ 73/864.63 X |

FOREIGN PATENT DOCUMENTS 257858  11/1969  U.S.S.R. ........................ 73/864.65

Primary Examiner—Tom Noland
Attorney, Agent, or Firm—Gloria K. Koenig

[57] ABSTRACT

A device for sampling remotely either liquid or solid from the bottom of a tank or other container is provided. The device comprises an outer cylindrical body of a relatively dense material having a suspending handle and a central opening through which a piston assembly is positioned and including an enlarged portion of the central opening functioning as a liquid sampling chamber. A piston assembly provided at the upper end with a piston rod and at the lower end with an enlarged piston head is positioned within and from the bottom of the central body opening with the enlarged piston head engaging at its top the bottom of the sampling chamber. The piston assembly is held within the body by a cylindrical sleeve element which is threaded into the lower portion at the body and is adapted to core out a sample of solid deposits. The piston head contains an "O" ring which at the bottom of the piston stroke engages the lower portion of the inner tapered bore of the cylindrical sampling element thereby closing the liquid sampling chamber. The device is suspended at the top in either a liquid or solid sampling mode depending on the specimen desired and lowered by gravity into the container from which a sample is to obtained.

6 Claims, 2 Drawing Sheets

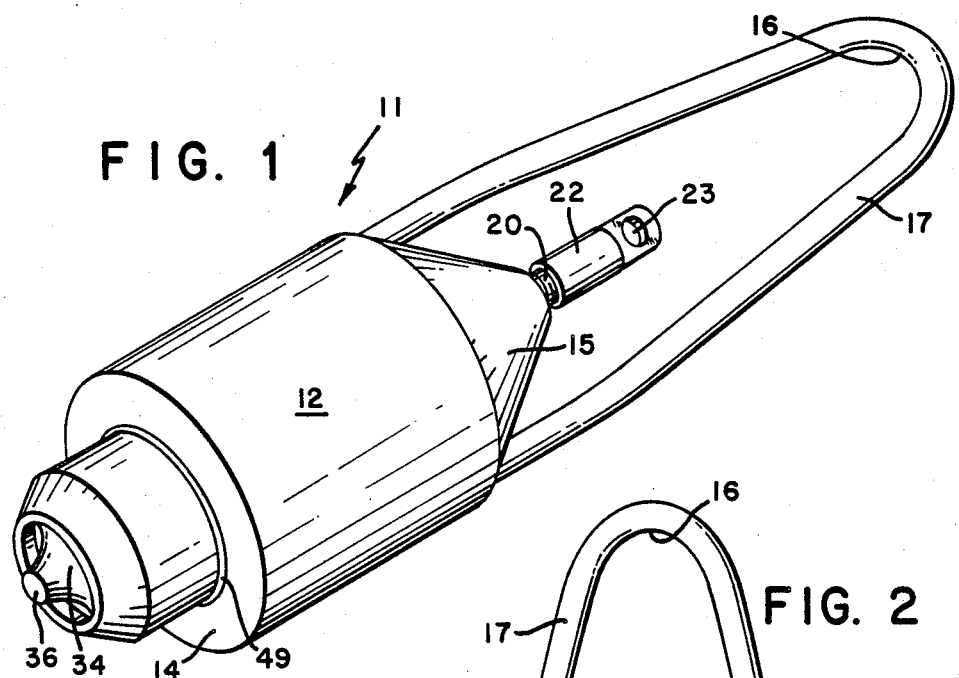
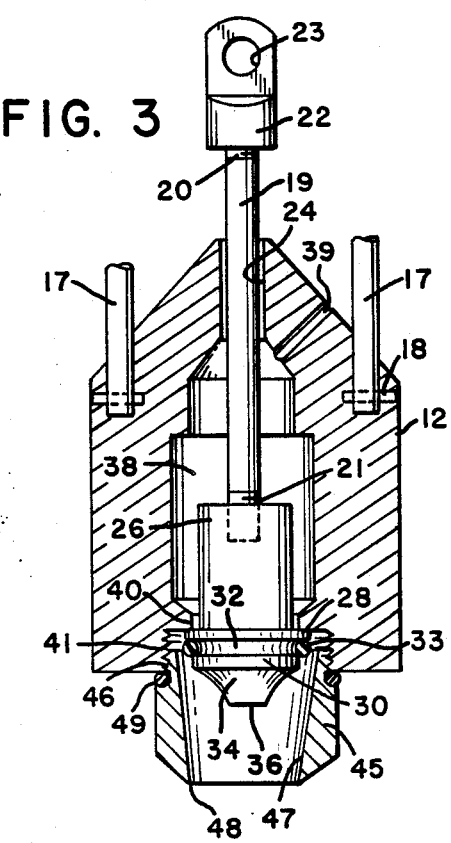
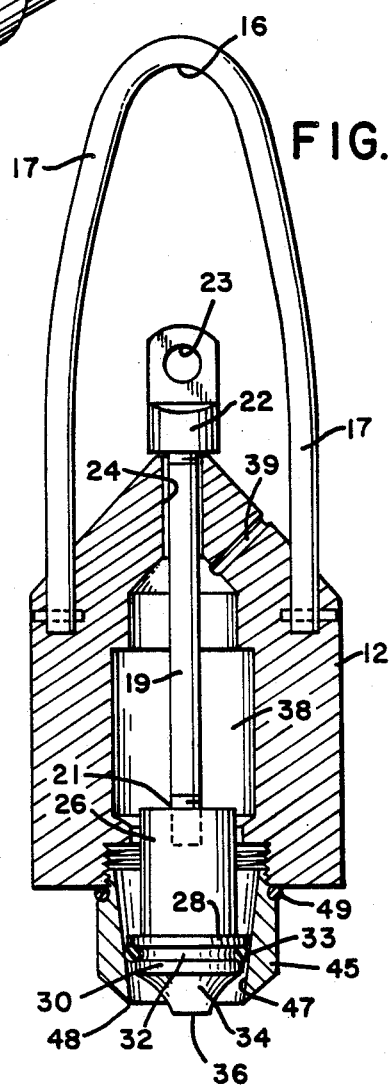

TANK BOTTOM SAMPLING DEVICE

This invention relates to an improved device for obtaining a sample of a liquid or of a solid or sludge material from the bottom of container such as a storage or shipping tank, e.g. an oil tanker, in which the place from which the sample is to be taken is not easily accessible.

BACKGROUND OF THE INVENTION

In many instances, for practical reasons, it is important to know the composition of a substance at the bottom of a container such as a tank, and because of the inaccessible location or massive size of the container, access to such "bottoms" is difficult. For example, before a tank is refilled, it may be essential to know the bottom composition because it may adversely affect the composition being introduced or the amount being charged. In the case of crude or refined liquid petroleum products, it could be of substantial economic disadvantage if the buyer believes he is purchasing a petroleum product and finds that he has purchased a significant amount of water which has settled at the bottom of the tank. Additionally, it may be important to determine whether the presence of a deleterious or unwanted "bottoms" substance is attributable to the buyer or to the seller or to the shipper. In addition to liquid sampling, it is sometimes important to obtain a sample of non-liquid substances such as a heavy petroleum residue or tar which settles at the bottom of a tank to study its composition to determine whether the product is contaminated or material introduced therein will be contaminated by the presence of such bottoms. For these and other known reasons such as those noted in U.S. Pat. No. 4,406,171 for determining the composition of tank bottoms, the present invention affords an improved and effective device for obtaining such sampling.

SUMMARY OF THE INVENTION

The present invention affords a simple device to be lowered by gravity into a tank, and upon contact with the tank bottom to obtain a sample of the liquid or non-liquid substance which is present contiguous to the tank bottom and to permit retrieval of such sample for analysis.

The device comprises a main cylindrical body which is formed of a relatively heavy material which has a specific gravity relatively greater than water so that the device upon lowering into a tank containing a liquid or semi-liquid material readily sinks to the bottom of the tank where the sample is to be obtained. The body may be formed of steel, brass or other suitable composition which is resistant to deterioration from contact with the sampling use environment. The main body may be suitable tapered at its upper end to enhance the upward movement of the device when it is being withdrawn. Affixed at the top of the main body is a suitable formed handle to which a cord or line may be secured for lowering and raising the device in the tank.

An opening is formed through the center of the main body into which a cylindrical piston element is inserted from the bottom of the main body and with the upper end of the rod of the piston element extending through the central opening in the main body.

The central base of the main body is machined to have an enlarged cylindrical central segment which has a reduced diameter at top and at the bottom of this central segment.

The piston element comprises an elongated piston rod and a cylindrical head portion which is secured at the bottom of the piston rod. The enlarged head portion comprises an upper part which forms an abutting ledge which engages the bottom reduced diameter of the central opening forming the sample chamber in the main body. The piston head portion contains also an annual recess below the abutting edge into which a relatively flexible "O" ring of suitable composition, such as rubber or polytetrafluoroethylene, is inserted. The lowermost portion of the piston head portion is suitably reduced in diameter so as to provide an extension that readily passes through an annular piston retaining sleeve which is secured at the bottom of the main body while preventing the piston head from passing through the annular sleeve by the engagement of the outer diameter of the "O" ring with the tapered inner bore of the retaining sleeve. Means such as an opening near the top of the piston rod, or an adapter secured at the top of the piston rod with an opening or other means, is provided for securing a line or cord at the top of piston rod.

In use, when the device is to be applied in sampling a liquid, the device is held by a line securing handle on the device body as it is lowered to the tank bottom. As the extension at the bottom of the piston contacts a tank bottom, the piston with extension moves upward, relatively, within the main body of the device which continues descending until it also bottoms. The relative upward movement of the piston and head within the cylindrical sleeve disengages the "O" ring from contact with the inner base of the piston retaining ring allowing liquid to flow into the sampling chamber within the device. As the device is elevated from the tank bottom, preparatory to recovery of the sample, the piston remains in a relatively lower position; this relative movement carries the inner bore of the cylindrical sleeve into engagement with the "O" ring thereby trapping the liquid sample in the sample chamber. As the device continues to be raised, by force of gravity, the weight of the piston assembly continues maintaining a seal between the "O" ring and the inner bore of the sleeve whose opening is tapered to have a smaller diameter bore at the bottom to prevent passage of the "O" ring. This tapered interior bore in the locking sleeve readily admits the "O" ring through the opening at the top but because of the relatively smaller diameter of the bore at the bottom restricts passage of the "O" ring through the bottom of the sleeve. When the sampling device is removed from the tank or container, the liquid sample is retrieved from the sampling device by lifting the piston relative to the main body thereby allowing the sample to flow out of the bottom of the cylindrical sleeve.

When the device of the invention is to be employed to obtain a sample of a solids deposit which may be present at a tank bottom, the unit is lowered to the bottom by suspending it from the central piston rod. In this position the piston is elevated relative to the main body of the sampler. The upward travel of the piston relative to the main body is stopped by the abutment of the annular ledge on the piston head with the reduced diameter formed in the central bore formed in the main body at bottom of the sample chamber. The effect is an opening at the bottom of the device, i.e., an opening in the sleeve with the mouth of the opening facing down. As the sampling unit is lowered into a solid deposit which may be present at the bottom of the tank, the weight of the device carries the sleeve into the solids and "cores" out a sample. As the unit is elevated from the tank bottom by the line secured at the top of the piston rod, the weight of the main body relative to the piston maintains the open position at the bottom of the sleeve located at the bottom of the device. The entry of the sleeve into the deposit and coring out a sample from the deposit is facilitated by making a "knife" edge at the bottom of the cylindrical sleeve. The inadvertent loss by gravity of the sample of the collected, as the unit is elevated, is inhibited by the tapered bore. The bore formed in the interior of the sleeve tapers so as to have the relatively smaller diameter at the bottom. When the sample device containing the solid sample is withdrawn, i.e., lifted, from the tank, removal of the cored sample plug from the sampler device of the invention is effected by forcing the piston rod down relative to the main body, thereby expelling the cored sample plug from the sleeve opening.

BRIEF DESCRIPTION OF THE DRAWINGS

FIG. 1 is a perspective view of the device of the invention.

FIG. 2 is an elevational view partly in section showing the piston in the lowered position in which the liquid sampling chamber is closed.

FIG. 3 is a view similar to that of FIG. 2 in which the suspending handles are broken away and the piston is in the elevated position which would allow liquid to flow upward into the sample chamber.

DESCRIPTION OF THE PREFERRED EMBODIMENT

Figure 4:
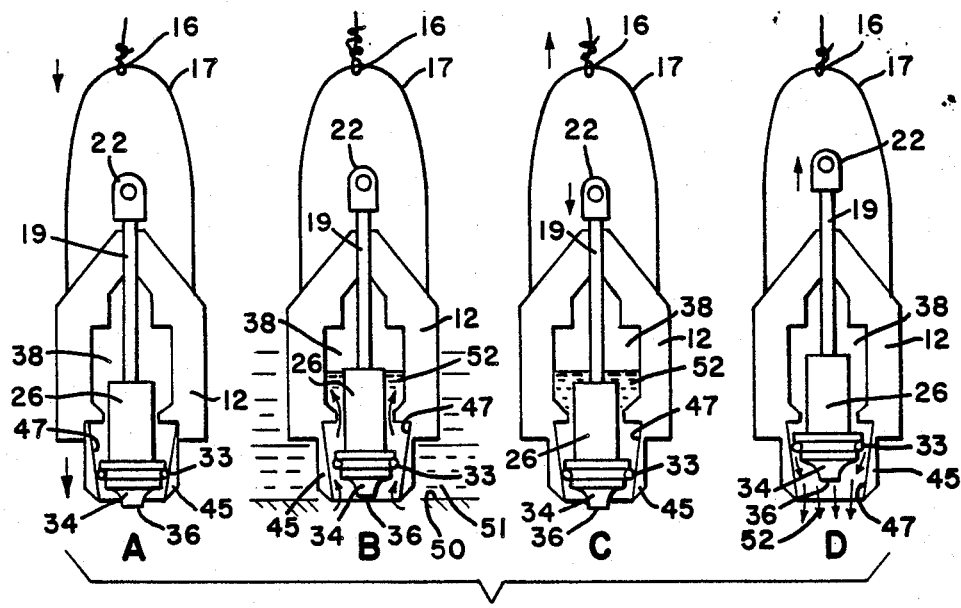
FIG. 4 illustrates schematically by steps A through D the use of the device of the invention in obtaining a bottoms liquid sample.

The sampling device 11 of the invention comprises a relatively simple yet rugged device with only a single moving part which is reliable and durable for use in obtaining a sample of a tank bottom substance.

The device 11 comprises a cylindrical body 12 which is provided throughout the length with an internal cylindrical passage 24 for accommodating a piston assembly member 19. The exterior of the body 12 may be conveniently formed with a flat bottom 14 and a top which may also be flat. Preferably, the top 15 is formed to have a cone-shape to minimize resistance as the device is withdrawn from a container or tank during the sampling operation. The opening 24 formed in the body 12 comprises a passage which extends throughout the body but varies in diameter to form a sampling chamber 38 and to accommodate a piston head 26 as described in more detail hereinafter.

The device is suitably supported with a handle 17 shown secured to the main body in a convenient manner as by pins 18 on the body 12. The handle is conveniently formed to be supported by a suspending line or cord at 16 and is shaped so as to clear the stroke of the piston 19 during the collection of a sample and allow the later evacuation from the device of the sample collected by the device by the manual actuation of the piston assembly which comprises the piston rod 19, adapter 22 and head 26.

The interior passage 24 in the main body 12 is formed as by machining a solid cylinder of a suitable noncorrosive material preferably a metal such as brass or stainless steel. However, the body 12 may also comprise a dense plastic composition e.g. nylon or polytetrafluoroethylene or blends of a plastic with or without a filler. The passage 24 is formed to provide a narrower upper portion forming a bearing for the piston rod 19, a relatively larger diameter segment providing a sampling chamber 38 bottoming in a restricted portion 40 against which the piston head 26 abuts at the top of the stroke of the piston assembly, and a bottom opening in which a retaining sleeve 45 is secured to the bottom of the main body. A vent opening for the chamber 38 is shown at 39.

The centrally located piston assembly, which comprises the single movable part relative to the body 12 in the course of use of the device of the invention, comprises a head arrangement 26 shown attached to the piston rod 19 such as by a thread connection 21 at the lower end of the piston. It will be understood, however, that the piston head portion 26 may be machined as an integral part of the piston inasmuch as this piston assembly may be inserted into the main body 12 from the bottom, i.e., by inserting the narrower piston rod 19 into the internal passage 24 of body 12 from the bottom and securing it with the sleeve retaining member 45.

The piston head 26 is formed so as to have an enlarged annular portion 28 which, as the piston is elevated in the body 12, engages the underside of the narrowed, i.e., restricted, portion 40 formed at the lower part of the sampling chamber 38, thereby limiting the upward movement of the piston in the body 12. Also formed in the piston head 26 below the expanded annular portion 28 is an annular recess 32 which accommodates a closure means for the sample chamber comprising a sealing O-ring 33 that fits and is held between annular portions 28 and 30; the latter being formed so as to be smaller in diameter than the annular portion 28 and yet to securely retain the "O" ring 33 therebetween. The lowermost portion 34 of the piston element is suitable shaped, such as in a taper, which facilitates assembly and does not interfere with movement of the piston head through a retaining sleeve element 45. The sleeve 45 is suitable fastened on the body 12 such as by an external threaded portion 46 on the sleeve 45 which mates with a corresponding threaded portion 41 formed internally at the bottom of central opening in the body 12. To enhance the seal between the mating threaded portions 41 and 46, an O-ring 49 of a suitable material, such as rubber or polytetrafluoroethylene may be placed in an annular recess for this purpose on sleeve 45 contiguous to the threaded portion 46. The bottom end of the piston head tapered portion 45, which engages the bottom of a tank when the device is lowered in a liquid sampling mode, is preferably flat. The piston 19 may be formed to have a uniform diameter at the top with a means (not shown) such as an opening to secure therein a line or cable to suspend the unit when lowering and raising the device in a solid sample collection mode, as will be discussed in more detail hereafter. Preferably, as shown, however, the piston rod is provided at the top with an adapter 22, conveniently secured such as by a threaded portion 20 to the rod 19, in order to afford more suitable means, i.e. larger, opening 23, to secure a suspending cord thereto and permit more convenient manual gripping to actuate the piston when expelling a collected sample.

The sleeve 45 is formed so as to have an internally tapered bore 47 which presents a relatively smaller diameter at the bottom than at the top of the sleeve 45.

The tapered internal bore 47 is dimensioned so as to allow unobstructed clearance of the piston head assembly with "O" ring 33 in place at the top of the inner bore of sleeve 45 but forms a tight seal between the lower part of the sleeve bore 47 and the O-ring 33. Although the lower part of bore 47 is sufficiently smaller to present a tight seal with the "O" ring 33, the opening at the bottom of the sleeve is preferably dimensioned so as to be sufficiently large to allow the piston head and piston assembly to pass through the sleeve 45 when the adapter 22 is removed from the top of the piston 19 and sufficient downward force is applied from the top of the piston rod to overcome the resistance of the O-ring 33 against the inner bore 47 of sleeve 45. It will be understood in this regard that the diameter of the annular part 28 of piston head 26 is dimensioned so as to be smaller in diameter than is the diameter of the bottom, i.e. of the narrowest diameter of the tapered bore 47 of sleeve 45. The bottom of sleeve 45 is preferably formed so as to have a "knife-edge" shape 48 at the bottom to facilitate its penetration of a tank bottoms material such as a sludge deposit.

Use of the device of the invention in collection a sample of (1) a liquid or fluid combination of liquid and sediments, and (2) a sample core of a more solid settled matter, e.g. sludge, from the bottom of a tank, will be described by reference to the schematic sequences of FIG. 4 and of FIG. 5, respectively.

Figure 5:
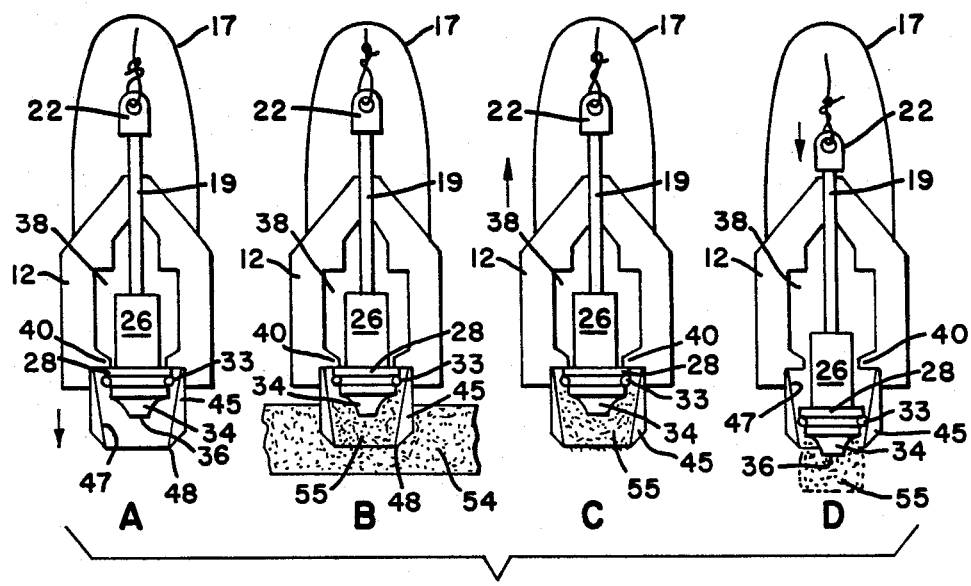
FIG. 5 illustrates schematically by steps A through D the use of the device of the invention in obtaining a bottom solid sample.

As seen by reference to FIG. 4, when a sample of a liquid or liquid mixture material present in a tank bottom is to be collected, the device suspended by a cord at 16 on handle 17 is lowered into the tank. When thus suspended, the piston assembly is positioned at a lower point in the sleeve 45 so that the "O" ring is in sealing engagement with the internal bore 47 of sleeve 45 as shown in sequence view A of FIG. 4. As the device is lowered into a tank and, as illustrated in sequence B of FIG. 4, the bottom 36 of the piston engages the tank bottom 50 containing a fluid material, such as water 51, the "O" ring 33 is disengaged from the inner bore 47 of sleeve 45 as the relatively heavy main body 12 of the device continues its descent to the bottom. The effect is to break the seal provided by the "O" ring 33 and allow a bottom sample to flow upward into the sample chamber 38 of the device. Thereafter, as the device is elevated, by lifting at the handle 17 suspended by a line or cable at 16, sequence view C of FIG. 4, the piston free of engagement with the tank bottom, moves down relative to the main body and effects a seal between the "O" ring and the inner wall 47 of sleeve 45 trapping the sample 52 of the liquid bottom material in the sample chamber 38. When the device has been withdrawn from the tank, the sample specimen 52 is collected from the device by holding the unit at handle 17 and raising the piston assembly by manually grasping the piston assembly at the adapter 22 and lifting it relative to the main body 12 of the device thereby expelling the sample 52 as illustrated in sequence view D of FIG. 4 and suitably analyzing the recovered sample 52.

When the device of the invention is used to collect a material which forms a solid sludge or aggregate, which is of a consistency that is capable of being recovered in a plug-like form, the manner of use is illustrated by reference to the sequence of view of FIG. 5. As illustrated in sequence A of FIG. 5, when used to collect a solid form material, the device is suspended by a cord or line at the top of the piston e.g. at the adapter 22. When thus held, the effect is to hold the piston assembly at the upper part of its stroke relative to the main body 12 whereby the top annular portion 28 of the piston head engages the narrowed bottom portion 40 of the sampling chamber 38. When thus supported, the interior area of the sleeve 45 forms a specimen collection area which, due to the relatively greater weight of the body 12 to the piston and head assembly that is supported at 22, maintains the open condition of the sleeve bore 47. As the device thus supported with the chamber open, is lowered into the sludge-like material, sequence view B of FIG. 5, the sleeve 45 embeds in the bottoms material 54 carried by the heavy weight of the device, coring out a sample 55. The tapered shape of the interior of the sleeve 45, with the mouth narrower than the upper portion, aids in retaining the collected core in the sleeve as the device is withdrawn from the tank. Upon being withdrawn, the device continues to be suspended at 22 at the top of the piston rod, sequence view C of FIG. 5, with no downward pressure from the piston head 26 on the collected sample 55. After the device has been recovered from the tank, the cored out sample 55 of the bottoms material is removed from the sleeve by holding the device at the handle 17 and forcing the cored plug 55 from the interior of the sleeve 45 by manually grasping the adapter 22 and pushing down on the piston relative to the main body 12.

While a preferred embodiment of the invention has been shown and described in detail, it will be understood that the invention comprises a substantially improved sampling device the details of which, except to the extent such details as are recited in the appended claims, should not be construed as limiting the invention.

What I claim is:

1. A device for use in withdrawing a sample of liquid and solid material which has settled in a container bottom, which comprises:
    (a) a cylindrical main body element provided with a lifting handle and a central cylindrical opening through the element, said central opening including:
        i. an upper portion to accommodate a piston rod,
        ii. a central portion having a relatively larger diameter than said upper portion and comprising a liquid sample chamber; and
        iii. a restriction at the bottom of the sample chamber against which a piston head abuts;
    (b) a piston assembly positioned in said central opening, said piston assembly, including:
        i. an upper rod segment which is slidably contained in the upper portion of the opening in the main body and contains contiguous to the top means to secure thereto a suspending line;
        ii. a piston head formed at a lower part of said piston rod and including an annular abutting portion which engages the restriction at the bottom of the sample chamber and limits the upward movement of the piston in the central opening;
        iii. an annular recess to accommodate an "O" ring formed in said piston head below said abutting portion, and an "O" ring contained therein; and
        iv. an extension depending below said annular recess and devised to engage a tank bottom from which a liquid sample is to be taken; and
    (c) a piston retaining sleeve with an interior bore tapering to a narrower interior opening secured at the bottom of said main body for receiving the piston head within the sleeve to provide a sealing engagement between the sleeve interior and the "O" ring of said piston head when said piston is at the lower position of its stroke.

2. The device of claim 1 in which the main body is formed so as to have an inverted cone shaped upper portion.

3. The device of claim 1 in which the upper segment of the piston rod is provided with an adapter for securing therein a suspending line.

4. The device of claim 1 in which the annular abutting portion of the piston head has a diameter smaller than the diameter of the narrowed portion of the interior bore of the piston retaining sleeve.

5. The device of claim 1 wherein the bottom of the piston retaining sleeve is formed with a sharp edge to facilitate penetration of a solids bed.

6. The device of claim 1 wherein the securing of the retaining sleeve on the bottom of the main body is enhanced with an "O" ring.

* * * * *